US008871512B2

(12) United States Patent
Carlson et al.

(10) Patent No.: US 8,871,512 B2
(45) Date of Patent: Oct. 28, 2014

(54) BIOCOMPATIBLE POLYMERIZABLE ACRYLATE PRODUCTS AND METHODS

(75) Inventors: William B. Carlson, Seattle, WA (US); Gregory D. Phelan, Cortland, NY (US); Phillip A. Sullivan, Seatlle, WA (US)

(73) Assignee: Empire Technology Development LLC, Wilmington, DE (US)

( * ) Notice: Subject to any disclaimer, the term of this patent is extended or adjusted under 35 U.S.C. 154(b) by 189 days.

(21) Appl. No.: 13/384,174

(22) PCT Filed: Oct. 27, 2010

(86) PCT No.: PCT/US2010/054267
§ 371 (c)(1),
(2), (4) Date: Jan. 13, 2012

(87) PCT Pub. No.: WO2012/057748
PCT Pub. Date: May 3, 2012

(65) Prior Publication Data
US 2012/0264214 A1    Oct. 18, 2012

(51) Int. Cl.
*C12N 5/00* (2006.01)
*A61L 27/18* (2006.01)
*C07H 13/04* (2006.01)
*C08F 20/18* (2006.01)
*C09J 133/14* (2006.01)
*A61L 27/52* (2006.01)

(52) U.S. Cl.
CPC ............... *C07H 13/04* (2013.01); *A61L 27/18* (2013.01); *C08F 20/18* (2013.01); *C09J 133/14* (2013.01); *A61L 27/52* (2013.01)
USPC ........... 435/396; 424/486; 424/487; 435/395; 435/399; 521/149; 525/54.2; 526/238.23

(58) Field of Classification Search
CPC ......... A61K 47/32; C08F 16/10; C08F 24/00; C08F 116/10; C08F 124/00; C08L 37/00; C12N 2533/30
USPC .................. 424/486, 487; 435/395, 396, 399; 521/149; 525/54.2; 526/238.23
See application file for complete search history.

(56) References Cited

U.S. PATENT DOCUMENTS

| 3,103,508 | A |  | 9/1963 | Fisher |  |
| 3,356,652 | A |  | 12/1967 | Kumar |  |
| 3,542,908 | A |  | 11/1970 | Sharples |  |
| 4,328,337 | A |  | 5/1982 | Kawasaki |  |
| 5,164,492 | A |  | 11/1992 | Kitazawa et al. |  |
| 5,854,030 | A |  | 12/1998 | Dordick et al. |  |
| 6,018,033 | A |  | 1/2000 | Chen et al. |  |
| 7,432,311 | B2 |  | 10/2008 | Mezzenga et al. |  |
| 2003/0194389 | A1 |  | 10/2003 | Porter |  |
| 2005/0129769 | A1 | * | 6/2005 | Barry et al. | 424/486 |
| 2006/0035341 | A1 |  | 2/2006 | Boeckh et al. |  |
| 2006/0246499 | A1 |  | 11/2006 | Spector et al. |  |
| 2009/0074832 | A1 |  | 3/2009 | Zussman et al. |  |
| 2009/0246259 | A1 |  | 10/2009 | Kita et al. |  |

FOREIGN PATENT DOCUMENTS

| CZ | 278551 | 3/1994 |
| GB | 1099372 | 1/1968 |
| JP | 09188691 | 7/1997 |
| JP | 2007206166 | 8/2007 |

OTHER PUBLICATIONS

Ting, S.R.S., et al.; Macromolecules, 2009, vol. 42, p. 9422-9434.*
Iwanaga, H., et al.; Fujifilm Research & Development, 2009, p. 43-47.*
Li, L., et al.; Journal of Materials Chemistry, 2009, p. 2789-2796.*
Ivirico, J. L. et al., "Proliferation and differentiation of goat bone marrow stromal cells in 3D scaffolds with tunable hydrophilicity", Journal of Biomedical Materials Research, Part B: Applied Biomaterials (2009), 91B(1), 277-286.
Granville A.M. et al., "Chemo-enzymatic Synthesis and RAFT Polymerization of 6-O-Methacryloyl Mannose: A Suitable Glycopolymer for Binding to the Tetrameric Lectin Concanavalin A?" Macromol. Symp. 2007, 255, 81-89.
Baba. A., "Synthesis of 1-β-O-acyl glucuronides of diclofenac, mefenamic acid and (S)-naproxen by the chemo-selective enzymatic removal of protecting groups from the corresponding methyl acetyl derivatives," Org. Biomol. Chem. (2006) 4, 3303.
Yang, Y. et al., "Electrospun Composite Mats of Poly[(D,Llactide)-co-glycolide] and Collagen with High Porosity as Potential Scaffolds for Skin Tissue Engineering," Macromolecular Materials and Engineering (2009), 294(9), 611-619.
Wang, Y, "Fabrication and characterization of a PAM modified PHBV/BG scaffold," Chinese Science Bulletin (2009), 54(17), 2940-2946.
Moshfeghian, A., "Characterization of emulsified chitosan-PLGA matrixes formed using controlled-rate freezing and lyophilization technique," Journal of Biomedical Materials Research, Part A (2006), 79A(2), 418-430.
Bokhari, M. et al., "Emulsion-templated porous polymers as scaffolds for three dimensional cell culture: effect of synthesis parameters on scaffold formation and homogeneity," J. Mater. Chem. (2007) 17, 4088.
The Freedonia Group Market Report: Specialty Adhesives US Industry Study with Forcasts to 2007 & 2012 (Apr. 2003).
Brown, MD, P. et al., "Comparison of N-Octyl-Cyanoacrylate vs Suture in the Stabilization of Cartilage Grafts" Arch Otolaryngology Head Neck Surg. 1996; 122(8):873-877 (Aug. 1996).
Jourdan, I.C, et al., "Initial Experience with the Use of n-Butyl 2-Cyanoacrylate Glue for the Fixation of Polypropylene Mesh in Laparoscopic Hernia Repair," Surgical Laparoscopy Endoscopy & Percutaneous Techniques. 8(4):291-293 (1998).

(Continued)

Primary Examiner — Robert Jones, Jr.
(74) Attorney, Agent, or Firm — Workman Nydegger

(57) ABSTRACT

Sugar-acrylic monomers are synthesized to have a carbohydrate moiety linked to an acrylate group. The sugar-acrylic monomers may be polymerized to form polymers, adhesives, hydrogels, and the like. The sugar-acrylic monomers and polymers may be used in tissue engineering, adhesives and sealers, wound healing, and the like.

21 Claims, No Drawings

(56) References Cited

OTHER PUBLICATIONS

Piñeros-Fernández, A. et al., "Octyl 2-Cyanoacrylate for Repair of Peripheral Nerve," Annals of Plastic Surgery, 55(2):188-195 (Aug. 2005).

Capt. Ralph A. W. Lehman et al., "Toxicity of Alkyl 2-Cyanoacrylates," AMA Arch Surg. 1966;93(3):441-446.

Vinters, H.V. et al., "The histotoxicity of cyanoacrylates," Neuroradiology (1985) 27(4), 279-291.

Bird, T. P. et al., "Preparation and derivatives of poly-(6-O-methacryloyl-D-galactose) and poly-(6-O-acryloyl-D-galactose)," Journal of the Chemical Society [Section] C: Organic (1966), (21), 1913-18.

Black, W. A. P. et al. "E. T. 6-O-Methacryloyl-D-galactose: a reactive, watersoluble monomer," Makromolekulare Chemie (1968), 117 210-14.

Kim, S. et al., Abstract for "Design of new biomimetic glycopolymers for hepatocellular engineering," Proceedings of the International Symposium on Controlled Release of Bioactive Materials (2000), 27th 638-639.

International Search Report and Written Opinion from International Application No. PCT/US2010/054267, dated Dec. 10, 2010.

\* cited by examiner

BIOCOMPATIBLE POLYMERIZABLE ACRYLATE PRODUCTS AND METHODS

BACKGROUND

Acrylic polymers have been used in the biomedical field to make cell growth media, tissue adhesives, and to promote wound healing. For example, cyanoacrylates have been used for several decades as tissue adhesives for the surface closure of wounds. However, toxic affects of the cyanoacrylates prevented their use inside of the wound. More recently acrylics and related nitriles, amides, and vinyl ketones such as 2-hydroxyethymethacrylate (HEMA), 2-hydroxypropylmethacrylate (HPMA), or acrylic functional derivatives of poly(ethylene glycol) (PEG) have been used as cell growth media and scaffold materials.

SUMMARY

Embodiments described herein relate to the synthesis, manufacture, and use of sugar-acrylates such as, but not limited to, sugar-methacrylate, sugar-acrylic, sugar-ethacrylate, sugar-trifluoromethacrylate, and sugar-cyanoacrylate. Acrylic derivatives of the sugars may be used in tissue engineering as cell growth media and structural materials, tissue sealers that can be used on either the surface or interior of tissue, and to manufacture environmentally benign adhesives.

In one aspect, a polymerizable acrylate product includes at least one polymerizable acrylate monomer having a pendant carbohydrate moiety linked to an acrylate group. The pendant carbohydrate moiety includes a derivative of a carbohydrate selected from allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, L-glycero-D-manno-heptose, or a combinations of these.

In one embodiment, the present disclosure provides an acrylate monomer having the formula (I):

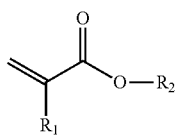

formula (I)

wherein $R_1$ is H, alkyl, aryl, heteroalkyl, heteroaryl, fluoro, chloro, bromo, hydroxyl, thio, ether, keto, aldehyde, azo, phosphine, arsine, $-CF_3$, or $-CN$, and $R_2$ is a carbohydrate derivative. In one embodiment, $R_2$ is selected from the group consisting of allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, L-glycero-D-manno-heptose or a derivative thereof.

Embodiments relate to sugar-acrylic hydrogel products and methods for making sugar-acrylic hydrogel products. In one aspect, the sugar-acrylic hydrogels are polymers formed from sugar-acrylic monomers. In one aspect, the sugar-acrylic hydrogel comprises a repeating unit having the formula (II):

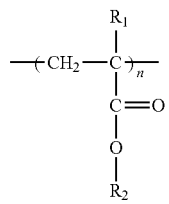

formula (II)

wherein $R_1$ is H, alkyl, aryl, heteroalkyl, heteroaryl, fluoro, chloro, bromo, hydroxyl, thio, ether, keto, aldehyde, azo, phosphine, arsine, $-CF_3$, or $-CN$, and $R_2$ is a carbohydrate derivative. In one embodiment, $R_2$ is a carbohydrate selected from a group consisting allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, L-glycero-D-manno-heptose, or a derivative thereof.

The methods include providing (1) a polymerizable monomer having a carbohydrate moiety linked to an acrylate group and (2) polymerizing at least the polymerizable monomer to yield a hydrogel. The method may include the addition of a crosslinking moiety to the polymerizable monomer having a carbohydrate moiety to control swelling of the hydrogel.

In one aspect, products utilizing derivatives of acrylic functional sugars incorporate the sugar-acrylic monomers, materials, structures, polymers, or hydrogels. The sugar-acrylic hydrogel products that can be manufactured using sugar-acrylic monomers may be tissue scaffolding materials, cell growth mediums, tissue adhesives, wound suture materials, healing promoter materials, engineered tissues, emulsion-templated porous polymers, tissue sealants, or the like.

Embodiments relate to methods for forming a biocompatible polymer scaffolding, including providing a first polymerizable monomer having a carbohydrate moiety functionalized with an acrylic moiety. The scaffolding may be made by utilizing a template formed using nano/microparticles and injecting the template with the polymerizable sugar-monomer and polymerizing the sugar-acrylic monomer in the template structure formed of the nano/microparticles. Removing the nano/microparticles yields a porous biocompatible scaffolding made from the sugar-acrylic polymer, structure, material, and/or hydrogel. The sugar-acrylic polymer can be either straight chained, branched, or crosslinked. The nano/microparticles can be made from any material that can be properly sized, is not soluble in the monomer media, and extracted from the polymerized acrylic-sugar monomer that forms the scaffold. In one embodiment, the nano/microparticle includes (poly)methylmethacrylate (PMMA) and may be removed from the polymerized monomer using an organic solvent such as acetone. In another embodiment, the nano/microparticle includes a salt, such as sodium chloride (NaCl), and may be removed from the polymerized sugar-acrylic monomer using water. In another embodiment, the nano/microparticle includes a salt, such as sodium iodide (NaI), and may be removed from the polymerized sugar-acrylic monomer using an organic solvent such as acetone. In another embodiment, the nano/microparticle includes paraffin, a wax, and may be removed from the polymerized sugar-acrylic monomer using an organic solvent such as acetone.

Embodiments relate to methods for forming an emulsion-templated porous polymer (e.g., a high internal phase emulsion composition). The emulsion-templated porous polymer may be manufactured by dissolving one or more sugar-acrylic monomers in an aqueous phase and combining the aqueous phase with an organic or oil phase and a surfactant to yield an intermediate reaction mixture. The one or more sugar-acrylic monomers in the intermediate reaction mixture may be polymerized to yield the emulsion-templated porous polymer.

Embodiments relate to methods for forming a hydrogel scaffold using a one or more sugar-acrylic monomers. The methods for making the hydrogel scaffold may include providing a first polymerizable monomer having a carbohydrate moiety linked to an acrylic moiety. The method may include forming a fibrous mat by simultaneously crosslinking and electro-spinning the polymerizable monomer.

Embodiments relate to methods for making a sugar-acrylic adhesive or sealer composition. The methods may include providing a first polymerizable monomer having carbohydrate moiety linked to an acrylic moiety; and dissolving the first polymerizable monomer in a solvent. The solvent may be biocompatible if used for biological purposes. Examples of biocompatible solvents include, but are not limited to, ethanol, water, dimethyl sulfoxide, propylene glycol and any combination of these. Alternately, the solvent may be a zero VOC solvent if the sugar-acrylic is used to bond inanimate objects. Examples of zero VOC solvents include, but are not limited to acetone, methyl acetate, t-butyl acetate, p-chlorobenzotrifluoride, and combinations of these.

Embodiments relate to methods for making a sugar-acrylic monomer that results in a product in which one or more of the hydroxyl groups on the sugar have a protecting group. Such protected sugar-acrylic monomers can have utility in biocompatible fields such as bio-adhesive, cell growth scaffold, tissue engineering, or the protected sugar-acrylic monomers can have utility in industrial adhesives, paints, coatings, or injection molding where biocompatibility is not an issue. The carbohydrate-acrylic monomers by their nature have a plurality of hydroxyl groups. The hydroxyl groups can cause problems under certain circumstances. Under conditions in which the hydroxyl groups cause problems it is needed to place protection moieties on the hydroxyl groups. The methods may include (i) providing a carbohydrate having a plurality of hydroxyl groups, (ii) reacting such carbohydrate with a protecting group agent to yield a protected carbohydrate, and (iii) linking a polymerizable acrylic moiety to the protected carbohydrate to yield a polymerizable acrylic monomer having a pendant carbohydrate moiety. The polymerizable acrylic functionalized monomer may be either a methacrylate or a cyanoacrylate or any number of structures as described with respect to formula (I).

Embodiments relate to a biocompatible polymerizable cyanoacrylate product that includes at least one polymerizable monomer having a pendant carbohydrate moiety linked to a cyanoacrylate group. The pendant carbohydrate moiety includes a derivative of a carbohydrate. The carbohydrate derivative can include protecting groups on the hydroxyl moieties of the carbohydrate.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

The illustrative embodiments described in the detailed description and claims are not meant to be limiting. Other embodiments may be utilized, and other changes may be made, without departing from the spirit or scope of the subject matter presented herein. It will be readily understood that the aspects of the present disclosure, as generally described herein can be arranged, substituted, combined, separated, and designed in a wide variety of different configurations, all of which are explicitly contemplated herein.

Unless otherwise specified, the terms "sugar" and "carbohydrate" are used interchangeably herein.

I. SUGAR-ACRYLIC MONOMERS

In one embodiment, the present disclosure provides an acrylic monomer having a pendant carbohydrate moiety linked to an acrylic moiety through a linker.

The term "carbohydrate moiety" is defined broadly to encompass simple sugars, monosaccharides, disaccharides, oligosaccharides, and the like, whether linear, branched or macrocyclic, and the derivatives thereof. The carbohydrate moiety may be a derivative of a triose, tetrose, hexose, heptose or a pentose. For example, the carbohydrate moiety may be a derivative of a carbohydrate selected from allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose or L-glycero-D-manno-heptose, derivatives of these, or combinations of these. In one embodiment, the carbohydrate may be a derivative of one or more of the carbohydrates described herein with the proviso that the carbohydrate moiety is not a derivative of mannose or galactose.

The carbohydrate may include both hydroxyl functional groups and amine functional groups. In one embodiment, the carbohydrate moiety may be a carbohydrate in which one or more hydroxyl groups are derivitized into amide, ester, ether, silane, carbamate, ketal, acetal, hemiacetal, hemiketal, and/or carbonate. In one embodiment, the carbohydrate moiety may be a carbohydrate in which one or more amine groups are derivitized into amide, primary amine, secondary amine, tertiary amine, azo, azide, ester, silane, and/or carbamate.

The linker may be a direct bond linking the carbohydrate moiety to the acrylate group. Alternatively, the linker may incorporate a spacing group including, but not limited to, alkyl, aryl, amino, thio, phosphine, alkene, alkyne, azo, substituted or unsubstituted alkylene, ether, polyol, ester, amide, imide, or a combination of any of the above. In one embodiment, the linker may include an O-linkage in which an ester bond links the carbohydrate moiety to the acrylate group. Formula (IIb) below illustrates an O-linked linker separating the acrylic group and carbohydrate of formula (I):

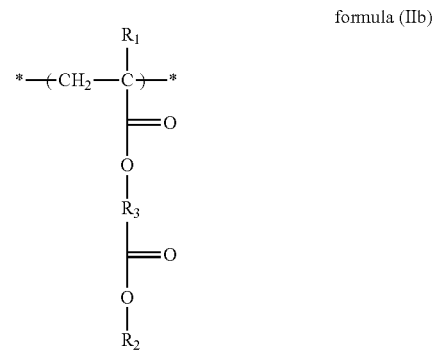

formula (IIb)

In formula (IIb) $R_1$ is H, alkyl, aryl, heteroalkyl, heteroaryl, fluoro, chloro, bromo, hydroxyl, thio, ether, keto, aldehyde, azo, phosphine, arsine, —CF$_3$, or —CN; R$_2$ is selected from the group of allose, altrose, glucose, mannose, gulose, idose, galactose, talose, psicose, fructose, sorbose, tagatose, ribose, arabinose, xylose, lyxose, ribulose, xylulose, erythose, threose, erythrulose, glyceraldehydes, altro-heptulose, L-glycero-D-manno-heptose, or a derivative thereof; and R$_3$ is a linker selected from alkyl, aryl, amino, thio, phosphine, alkene, alkyne, azo, substituted or unsubstituted alkylene, ether, polyol, ester, amide, imide, or a combination of these.

In one embodiment, the acrylate monomer has the formula (I):

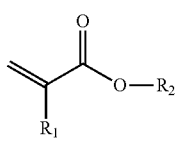

formula (I)

wherein R1 is H, alkyl, aryl, heteroalkyl, heteroaryl, fluoro, chloro, bromo, hydroxyl, thio, ether, keto, aldehyde, azo, phosphine, arsine, —CF$_3$, or —CN, and R$_2$ is a carbohydrate derivative. In one embodiment, R$_2$ is a carbohydrate selected from a group consisting allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, L-glycero-D-manno-heptose, or a derivative thereof. In one embodiment, the sugar-acrylic monomer, as shown in the structure (1), may include a mannose carbohydrate moiety:

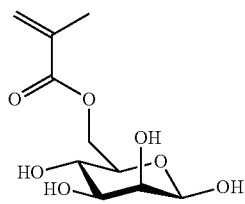

(1)

In another embodiment, the sugar-acrylic monomer, as shown in the structure (2), may include a β-D-N-acetylgalactosamine carbohydrate moiety:

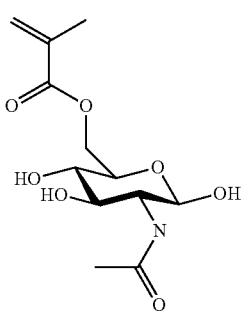

(2)

In one embodiment, the disclosure provides a biocompatible polymerizable acrylic product. The biocompatible polymerizable acrylic product includes at least one polymerizable acrylic monomer having a pendant carbohydrate moiety linked to an acrylate group through a linker. The polymerizable acrylate products may include polymerizable acrylate monomers that differ only in the linker. In addition, hydroxyl groups of the carbohydrate may be substituted for a halide such as chloride or bromide.

In yet another embodiment, the present disclosure relates to a biocompatible polymerizable cyanoacrylate product. The cyanoacrylate product includes at least one polymerizable monomer having a pendant carbohydrate moiety linked directly to a cyanoacrylate group or through a linker connecting the carbohydrate to the cyanoacrylate moiety.

In one embodiment, the sugar-cyanoacrylate monomer may have a structure as shown in Structures 10 through 17, shown below (where version "a" is the ring form and version "b" is the straight chain form):

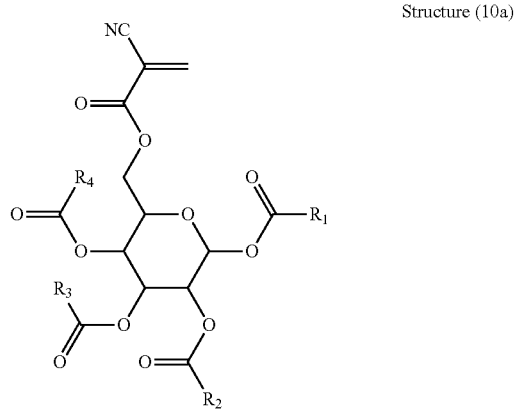

Structure (10a)

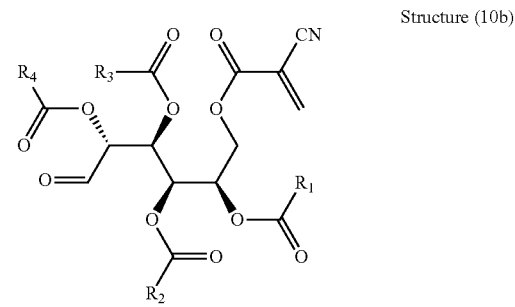

Structure (10b)

Where R$_1$, R$_2$, R$_3$, and R$_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, or L-glycero-D-manno-heptose. The sugar may be in cyclic form as shown in Structure (10a) or may be provided in straight chain form as shown in Structure (10b).

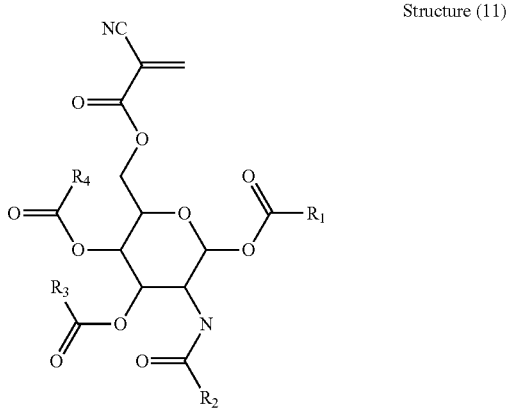

Structure (11)

Where $R_1$, $R_2$, $R_3$, and $R_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altroheptulose, L- or glycero-D-manno-heptose. The sugar may be in cyclic form, as shown in structure (11), or may be provided and/or converted to the straight chain form.

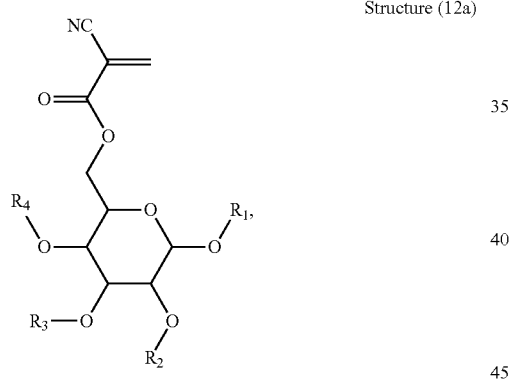

Structure (12a)

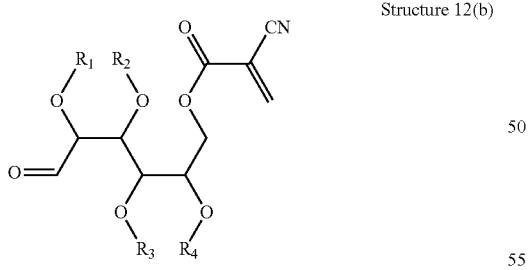

Structure 12(b)

Where $R_1$, $R_2$, $R_3$, and $R_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altroheptulose, L- or glycero-D-manno-heptose. The sugar may be in cyclic form as shown in structure (12a) or may be provided and/or converted to the straight chain form as shown in Structure (12b).

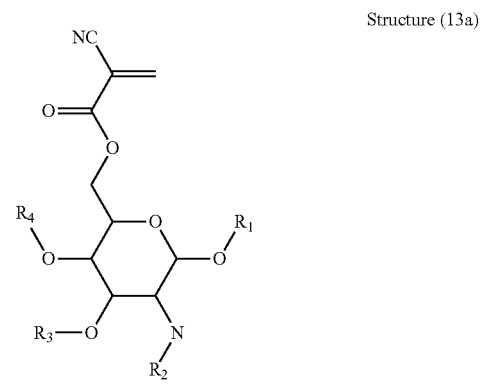

Structure (13a)

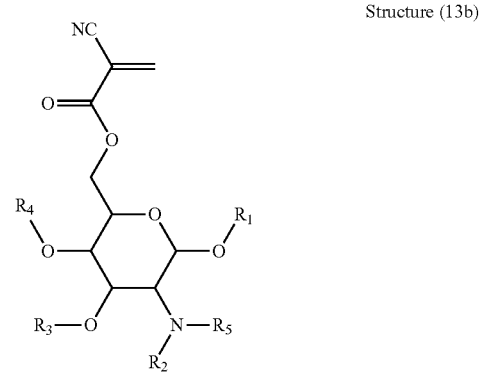

Structure (13b)

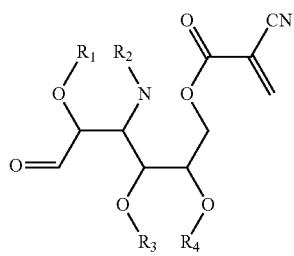

Structure (13c)

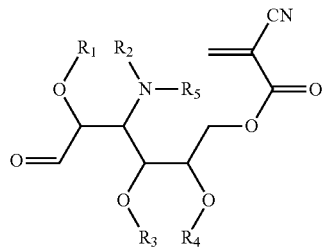

Structure (13d)

Where $R_1$, $R_2$, $R_3$, $R_4$ and $R_5$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altroheptulose, L- or glycero-D-manno-heptose. The sugar may be in cyclic form as shown in Structures (13a) and 13(b) or may be provided and/or converted to the straight chain form as shown in structure (13c) and (13d).

Structure (14)

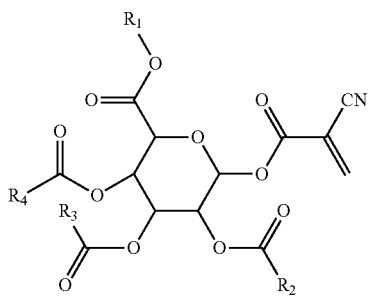

Where $R_1$, $R_2$, $R_3$, and $R_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altroheptulose, L- or glycero-D-manno-heptose The sugar may be in cyclic form (as shown in structure (14) or may be provided and/or converted to the straight chain form.

Structure (15)

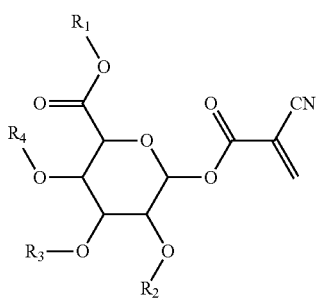

Where $R_1$, $R_2$, $R_3$, and $R_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, L- or glycero-D-manno-heptose The sugar may be in cyclic form, as shown in structure (15), or may be provided and/or converted to the straight chain form.

Structure (16)

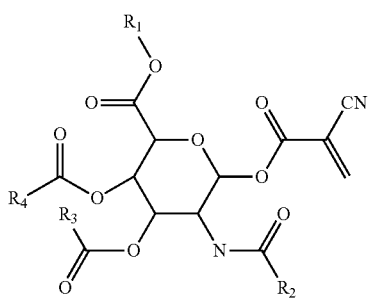

Where $R_1$, $R_2$, $R_3$, and $R_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altroheptulose, L- or glycero-D-manno-heptose The sugar may be in cyclic form, as shown in structure (16), or may be provided and/or converted to the straight chain form.

Structure (17)

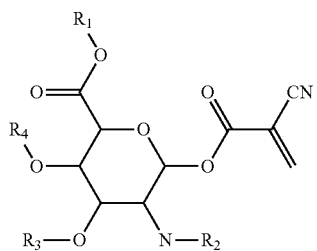

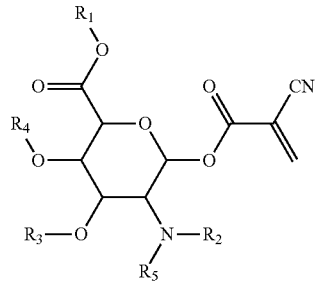

Where $R_1$, $R_2$, $R_3$, and $R_4$ are independently an alkyl, heterocycle, cycle, carbocycle, or any atom other than hydrogen and the sugar may be allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altroheptulose, L- or glycero-D-manno-heptose The sugar may be in cyclic form, as shown in structure (17), or may be provided and/or converted to the straight chain form

II. SUGAR-ACRYLIC POLYMERS

The present disclosure further discloses sugar-acrylic polymers incorporating the sugar-acrylic monomers described herein. The polymer may be a block copolymer, a random copolymer, alternating copolymer, or a graft copolymer of two or more monomers copolymerized together. Examples of monomers that can be copolymerized with the sugar-acrylic monomers but not limited to such monomers are hydroxyethyl (meth)acrylate, hydroxypropyl (meth)acrylate, styrene, acrylamide, vinyl acetate, vinyl methacrylate, methylvinylether, trifluoromethylvinylether, N-vinylpyrrolidone, methylvinylketone, and maleic anhydride. Monomers with more than one functionality can also be used with the sugar-acrylic monomers to create crosslinked polymer networks and thermosetting resins. Examples of monomers that can be used to crosslink the sugar-acrylics but not limited to are divinylbenzene, ethylene glycol di(meth)acrylate, poly(ethylene glycol) di(meth)acrylate, and glycerol tri(meth)acrylate. In one embodiment, the second or additional monomer may be any type of acrylic. In another embodiment, the second or additional monomer may be a sugar-acrylic monomer.

In one embodiment, the present disclosure provides a hydrogel comprising a sugar-acrylic polymer. The sugar-acrylic polymer may include a repeating unit having the formula (II):

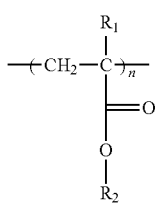

formula (II)

wherein n is an integer from 1 to 10,000, $R_1$ is H, alkyl, aryl, heteroalkyl, heteroaryl, fluoro, chloro, bromo, hydroxyl, thio, ether, keto, aldehyde, azo, phosphine, arsine, —$CF_3$, or —CN, and $R_2$ is a carbohydrate derivative. In one embodiment, $R_2$ is a carbohydrate selected from a group consisting allose, altrose, glucose, mannose, gulose, idose, galactose, talose, psicose, fructose, sorbose, tagatose; ribose, arabinose, xylose, lyxose, ribulose, xylulose, erythose, threose, erythrulose, glyceraldehydes, altro-heptulose, L-glycero-D-mannoheptose, or a derivative thereof.

In one embodiment, the hydrogel may include a sugar-acrylic polymer having the following structure 3:

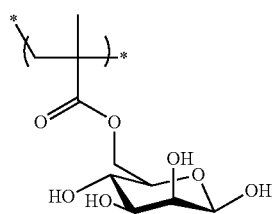

Structure (3)

In one embodiment, the two or more sugar-acrylic monomers may be selected to produce a hydrogel polymer that mimics hyaluronic acid. For example, in one embodiment, a glucose methacrylate may be copolymerized with a β-D-N-acetylgalactosamine methacrylate monomer to yield a pseudo hyaluronic acrylic polymer hydrogel, which is illustrated below in Structure (4).

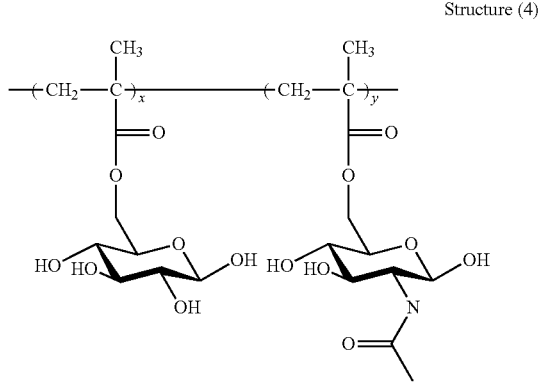

Structure (4)

where x and y may independently be between 0.0001 to 99.9999. In one embodiment x and y may be about 0.5 and 0.5 respectively and the carbohydrates can be alternating gluconic acid and β-D-N-acetylgalactosamine so as to form a hyaluronic acid.

The polymers provided in the present disclosure may be used as a tissue scaffolding material or for tissue engineering as described more fully below.

III. METHODS FOR MAKING SUGAR-ACRYLIC MONOMERS

Embodiments of the present disclosure relate to the synthesis, manufacture, and use of sugar-acrylic and polymers manufactured from the monomers. The sugar-acrylic monomers may be manufactured from a carbohydrate substrate and a vinyl acrylic compound (vinyl acrylate, vinyl methacrylate) that, when reacted together, yield an acrylate monomer having a pendant carbohydrate moiety.

The carbohydrate substrates used in the methods described herein may be selected from any biocompatible carbohydrate capable of reacting with an acrylate molecule to form an acrylic with pendant carbohydrate moiety. The carbohydrate substrate may be a monosaccharide such as a carbohydrate having a triose, tetrose, heptose, hexose or a pentose base structure. Examples of suitable carbohydrates include, but are not limited to allose, altrose, glucose, mannose, gulose, idose, galactose, talose, psicose, fructose, sorbose, tagatose, ribose, arabinose, xylose, lyxose, ribulose, xylulose, derivatives of these, and combinations of these. The carbohydrate substrate may be in its straight chain or cyclic form. In some embodiments, the carbohydrate may be any carbohydrate disclosed herein or a combination thereof with the proviso that the carbohydrate substrate is not mannose or galactose.

The vinyl acrylate compound may be any molecule having a carbon-carbon double bond and an ester group bonded to one of the double bonded carbons, so long as the acrylate compound is capable of reacting with the carbohydrate substrate to produce a polymerizable monomer having a pendant carbohydrate moiety. Non-limiting examples of suitable vinyl acrylate compounds that can be useful in synthesizing sugar-acrylic monomers include vinyl acrylate, vinyl methacrylate, methyl methacrylate, vinyl ethacrylate, methyl ethacrylate combinations of these and the like.

The reaction of the vinyl acrylate compound and the carbohydrate can be carried out using solvents, catalysts, free radical inhibitors, and/or heat according to techniques known in the art. For example, the reaction between a vinyl acrylate compound and a carbohydrate substrate may be carried out by dissolving the carbohydrate substrate and the vinyl acrylate compound in one or more solvents and then reacting the ester of the vinyl acrylate with a hydroxyl of the sugar.

The solvent may be selected for its compatibility with the vinyl acrylate compounds, carbohydrate substrate, enzymes, and free radical inhibitors. Example solvents include water, alcohol, and/or organic solvents (e.g., acetone). The reaction may be catalyzed using an enzyme or other suitable catalyst. An example of an enzyme catalyst that may be used includes, but is not limited to, *Candida Antarctica* lipase immobilized polymer. Molecular weight of the sugar-acrylic polymers may be controlled by the use of chain transfer agents; an example of which are mercaptans. The reaction may be carried out in a range from about 30° C. to about 85° C. depending upon the initiators used.

Following the reaction of the vinyl acrylate molecule and the carbohydrate group, the resulting monomer may be purified using any purification technique, including, but not limited to, chromatography (e.g., flash chromatography) or distillation. Chromatography may be performed to separate the desired reaction products from side reaction products.

The present disclosure also relates to methods for making a biocompatible sugar-acrylic product where one or more of the hydroxyl groups on the sugar derivative have a protecting group. The method may include (i) providing a carbohydrate having a plurality of hydroxyl groups, (ii) reacting the carbohydrate with a protecting group agent to yield a protected carbohydrate, and (iii) linking a polymerizable acrylate group to the protected carbohydrate to yield a polymerizable acrylate monomer having a pendant carbohydrate moiety.

In a first embodiment, the method of making the protected sugar-acrylic monomer relates to making a cyanoacrylate monomer, polymer, or product. The method includes providing a carbohydrate substrate suitable for reacting with a protecting group agent to yield a protected carbohydrate. The carbohydrate substrate includes a plurality of hydroxyl groups. The carbohydrate substrate may be a hexose or pentose or a carbohydrate selected from allose, altrose, glucose, mannose, gulose, idose, galactose, talose, psicose, fructose, sorbose, tagatose, ribose, arabinose, xylose, lyxose, ribulose, xylulose, or a derivative of these, or a combination of these. The carbohydrate substrate may be a straight chain or a cyclic carbohydrate.

The protecting group agent may be any agent capable of reacting with an active hydrogen atom of the carbohydrate substrates to form a reaction product with at least a portion of the hydroxyl groups protected. Protecting groups include amide, ester, ether, silane, carbamate, ketal, acetal, hemiacetal, hemiketal, carbonate, and combinations of these. The protecting agent may be an acetylation agent such as, but not limited to, acetic anhydride.

The protecting group agent may be reacted with the carbohydrate substrate using reaction conditions known in the art. In one embodiment, a base (e.g., sodium hydroxide) is dissolved in a solvent (e.g., methanol) to which the carbohydrate substrate is added slowly and allowed to react to produce an intermediate carbohydrate substrate. The pH may be maintained above about 8 by adding additional base as needed. The solvent is removed from the intermediate carbohydrate substrate and acetylation carried out by reacting the intermediate carbohydrate substrate in a solvent to yield the protected carbohydrate. The protected carbohydrate may have acetyl groups or other organic groups that replace an active hydrogen on the carbohydrate substrate.

In one embodiment, the protected carbohydrate may have a structure as illustrated below.

Structure (5)

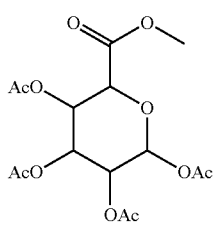

The protected carbohydrate is an intermediate compound used to manufacture sugar cyanoacrylates. The protected carbohydrate may be modified by directly attaching a cyanoacrylate group or by attaching a precursor to a cyanoacrylate and modifying the precursor molecule to yield the cyanoacrylate group.

In one embodiment, the method of making a sugar cyanoacrylate includes forming a second intermediate protected carbohydrate having a leaving group. The leaving group provides a site for reacting a precursor to a cyanoacrylate to the second intermediate protected carbohydrate to yield a third protected carbohydrate intermediate. For example, the protected carbohydrate may be reacted with an acid halide in acetic acid to yield a halide intermediate protected carbohydrate. The following structure is a non-limiting example of a halide intermediate protected carbohydrate.

Structure (6)

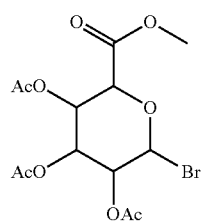

The second protected carbohydrate intermediate may be reacted with a cyanoacetate compound to form a third protected carbohydrate intermediate. For example, cyanoacetic acid and cesium carbonate (catalyst) may be mixed with the second protected carbohydrate intermediate to yield an alkyl cyanoacetate. An example of a alkyl cyanoacetate is shown below in structure (7)

Structure (7)

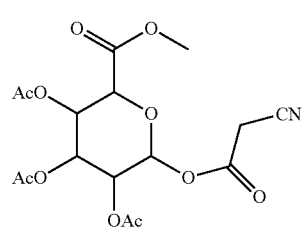

The third protected carbohydrate intermediate (e.g., alkyl cyanoacetate) may be condensed (e.g., using formaldehyde) to produce an oligomer shown below in Structure (8)

Structure (8)

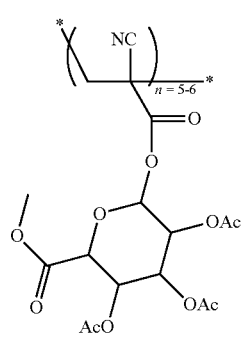

The cyanoacetate oligomers may then be thermally depolymerized (i.e., "cracked) to produce a polymerizable sugar-acrylic monomer.

A non-limiting example of a sugar-acrylic monomer is shown in the structure (9).

Structure (9)

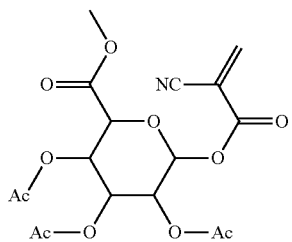

Those skilled in the art will recognize that there are other synthesis routes for adding a cyanoacrylate group to an intermediate protected carbohydrate.

The methods of the disclosure also relate to methods for making sugar-acrylics such as sugar methacrylate or other polymerizable sugar-acrylic monomer. The monomers may be polymerized via thermal, photo-chemical, or catalytic means. The monomers manufactured according to this embodiment may have protected carbohydrate moieties or may have the protecting groups removed from the intermediate to yield unprotected sugar-acrylic products.

In one embodiment the method may include (i) providing a carbohydrate having a plurality of hydroxyl groups, (ii) reacting the carbohydrate with a protecting group agent to yield a protected carbohydrate, and (iii) linking a polymerizable acrylic group to the protected carbohydrate to yield a polymerizable acrylate monomer having a pendant carbohydrate moiety.

In one embodiment, an intermediate protected carbohydrate is reacted with a methacrylate moiety to produce a polymerizable acrylic monomer of the methacrylate genus having a protected carbohydrate moiety. The intermediate protected carbohydrate to be bonded to the methacrylate molecule may be made according to any of the methods described herein so long as the intermediate protected carbohydrate includes at least one functional group suitable for forming a bond with the methacrylate molecule or a precursor thereof. In one embodiment, the intermediate protected carbohydrate may be an intermediate protected carbohydrate having a leaving group. The leaving group may be a halogen leaving group. A non-limiting example of a suitable intermediate protected carbohydrate that may be used in the method of making the protected carbohydrate methacrylate is shown in Structure (18) below.

Structure (18)

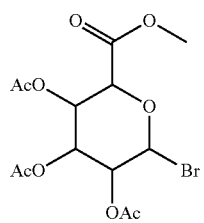

An acrylic group (e.g., a methacrylate) is bonded to the intermediate protected carbohydrate. In one embodiment, the acrylate group may be a produced by reacting the protected carbohydrate with an acrylic molecule. The acrylic molecule may include the polymerizable acrylic group or a precursor to the polymerizable acrylic group (i.e., one or more additional reaction steps may be used to make the precursor polymerizable). Examples of suitable acrylic molecules include such as, but not limited to acrylic acid, methacrylic acid, ethylacrylic acid, methyl methacrylic acid, and the like.

The reaction of the acrylic molecule with protected carbohydrate intermediates allows the reaction to be carried out using reagents that would not be compatible with hydroxyl groups. In addition, the location of the linkage between the protected carbohydrate and the acrylate molecules may be selected by selecting the reactive group (e.g., the leaving group) at the position where the desired linkage should occur. The reaction may be carried out in an aprotic solvent such as, but not limited to DMF, acetic acid, pyridine, acrylic acids, triethylamine, THF or DMSO. In one embodiment, the reaction linking the acrylic group and the protected carbohydrate intermediate may be carried out using cesium carbonate in DMSO to yield a protected polymerizable sugar-acrylic monomer. An example of a acrylate monomer manufacture according to this method is shown in Structure (19)

Structure (19)

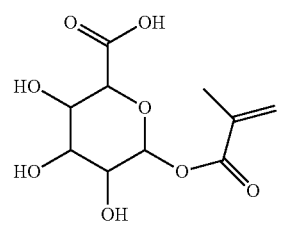

Once the polymerizable acrylic group is bonded to the carbohydrate moiety, the protecting group may be removed. For example, unprotecting the carbohydrate moiety may be desired to make the sugar-acrylic monomers more hydrophilic. The unprotecting of the carbohydrate moiety may be carried out using techniques known in the art. For example, deprotection of acetyl protecting groups may be carried out using a dilute solution of hydrochloric acid or selectively carried out using lipase AS Amano (LAS) and an esterase (e.g., from porcine liver).

Methods for Making Polymers

The disclosure also relates to methods for making sugar-acrylic polymer products. In one embodiment, the sugar-acrylic polymer products include a sugar-acrylic hydrogel. The hydrogel may be a water-swellable polymeric matrix having a three-dimensional network of macromolecules of sugar-acrylic polymers held together by covalent or non-covalent crosslinks. The sugar-acrylic hydrogel can absorb water through the interaction between water molecules and the carbohydrate moieties.

The methods may include providing a first polymerizable monomer having a carbohydrate moiety linked to an acrylate group. The polymerizable monomer can be any sugar-acrylic monomer described herein, including, but not limited to sugar-acrylic monomers having a carbohydrate moiety that is a derivative of hexose or pentose a derivative of a carbohydrate selected from allose, altrose, glucose, mannose, gulose, idose, galactose, talose, psicose, fructose, sorbose, tagatose, ribose, arabinose, xylose, lyxose, ribulose, xylulose, or a combination of these. The carbohydrate moiety may include a straight chain carbohydrate or a cyclic carbohydrate. In one embodiment at least a portion of the sugar-acrylic monomers are not functionalized with an amino acid.

Polymerization may be carried out by a thermal, photochemical, or catalytic polymerization to produce a plurality of sugar-acrylic polymer molecules. In one embodiment, polymerization may be carried out using an initiator. The initiator may be light cured (e.g., UV cured) or thermally cured. Example of a suitable initiators include, but is not limited to, AIBN, benzoyl peroxide, persulfate, hydrogen peroxide, and 2-hydroxy-2-methyl-1-pheyl-propan-1-one (Darocure 1173).

The polymerization reaction may be carried out using a crosslinking agent. Examples of suitable cross-linking agents include molecules having two or more polymerizable groups that can be incorporated into the growing acrylate chain. Suitable cross-linking agents include dimethacrylates, such as, but not limited to ethylene glycol di(meth)acrylate, poly(ethylene glycol) di(meth)acrylate, sugars with more than one acrylic, divinylbenzene, glycerol tri(meth)acrylate. Alternatively, or in addition, cross-linking may be carried out using other types of cross-linking agents, including cross linking that occurs between pendant groups of the polymer carbon backbone. The extent of crosslinking can be controlled to provide a hydrogel with a desired level of swelling.

The acrylic polymers may also be manufactured using two or more monomers to form protected or unprotected sugar-acrylic copolymers. The second or additional monomer may be any type of acrylic class of monomers, including any methacrylate. The additional monomer(s) can be from other polymerizable classes exemplified but not limited to such monomers are hydroxyethyl (meth)acrylate, hydroxypropyl (meth)acrylate, styrene, acrylamide, vinyl acetate, vinyl methacrylate, methylvinylether, trifluoromethylvinylether, N-vinylpyrrolidone, methylvinylketone, and maleic anhydride. The second or additional monomer may be a sugar-acrylic monomer. In one embodiment, the two or more sugar-acrylic monomers are selected to produce a biocompatible polymer that mimics hyaluronic acid. For example, in one embodiment, a β-D-gluconic acid methacrylate monomer is copolymerized with a β-D-N-acetylgalactosamine methacrylate monomer to yield a pseudo hyaluronic acrylic polymer. A non-limiting example of a copolymer with deprotected carbohydrate moieties is shown below in structure (20):

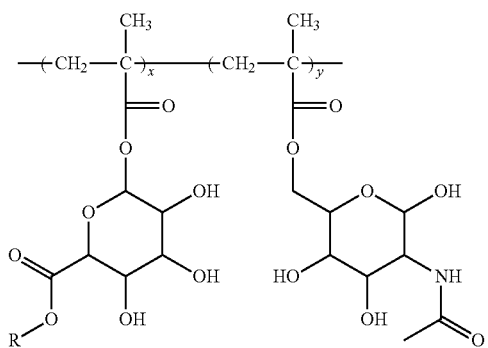

Structure (20)

IV. SUGAR-ACRYLIC ADHESIVES AND SEALANTS

The present disclosure relates to sugar-acrylic products incorporating the polymerizable sugar-acrylic monomers described herein. The sugar-acrylic products may be a tissue adhesive or sealer compositions or an environmentally benign adhesive. The sugar-acrylic adhesives or sealers may be provided as a sugar-acrylic monomer or may be provided as a sugar-acrylic polymer dissolved in a solvent.

Tissue sealers or adhesives may include, but are not limited to substances, compositions, materials or objects that can form, reinforce, or strengthen any type of bond, attachment, seal, connection, communication, or other physical association between any tissue, organ, structure or other part of an organism and any other substance, composition, or object. The substance, composition, or object can be any type of substance, cell, composition, or object, or combination or composites thereof including, but not limited to: one or more portions of the same tissue, organ, structure or part of the organism; one or more different tissues, organs, structures, or parts of the same organism; one or more other organisms; one or more tissues, cells, organs, structures, or parts of one or more other organisms; one or more synthetic or inanimate compositions, substances, or objects (e.g. medical devices, prosthetics, implants, carriers for delivery of a pharmaceutical, nutraceutical, or other substance), or portions thereof; and any combination or composite of one or more of the foregoing. The tissue adhesives and sealants also include materials and substances that can serve as glues or adhesives. The terms sealers and adhesives may be used to cover, obstruct, fill, or seal any type of wound, ulcer, injury, hole, leak, cavity, enclosure, or opening in any tissue, organ or part of any organism as well as any composition, substance, or object that can have a hemostatic effect or can otherwise prevent, reduce, or eliminate the leakage, flow, or release of any substance (including liquid, solid, semisolid, and gas) into or out of the body of an organism or any part thereof. Sealants, tissue adhesives or tissue sealants can include, but are not limited to electroprocessed materials and matrices comprising electroprocessed materials.

In one embodiment, the tissue sealer or adhesive may be a tissue adhesive that is compatible with biological tissues. The tissue adhesive may include sugar-acrylic monomers that can be applied to the surface of the tissue and polymerized to connect and hold together the tissue and promote healing of said tissue. The polymerizable sugar-acrylic monomers used in the embodiments described herein may be cyanoacrylates or methacrylates. Cyanoacrylates may be advantageous since these molecules are initiated and can polymerize in the presence water, which is present in the atmosphere and/or on the tissues of a person. Thus, cyanoacrylate tissue adhesives and sealers may be used without an additional chemical initiator.

The tissue adhesives or sealers may include one or more solvents. The solvent may be selected to be compatible with the sugar-acrylic monomer by providing a desired solubility for the monomer. In addition, the solvent may also be selected to be biocompatible with the tissue to which the adhesive will be applied. The solvent may include alcohols, including methanol and ethanol, biocompatible acids such as formic acid, oils such as olive oil, peanut oil, ethylene glycol, water, DMSO, DMF, and combinations of these, and the like.

For adhesive and sealer products including cyanoacrylates, the solvent may be non-aqueous and/or aprotic to avoid premature polymerization of the monomers. The solvent may be mixed with the sugar-acrylic monomers in an amount ranging from about 2 wt % to about 80 wt % solvent, about 4 wt % to about 40 wt % solvent, or about 5 wt % to about 20 wt %. The sugar-acrylic monomers can have relatively high solubility in many different solvents due to the carbohydrate moiety.

The tissue adhesives and sealers taught herein may be used in any number of tissue repair applications, such as, but not limited to, seroma and hematoma prevention, skin and muscle flap attachment, repair and prevention of endoleaks, aortic dissection repair, lung volume reduction, neural tube repair and the making of microvascular and neural anastomoses. In the method of using the sugar-acrylic products, the repair of damaged tissue may be carried out within the context of any standard surgical process allowing access to and repair of the tissue, including open surgery and laparoscopic techniques. Once the damaged tissue is accessed, the polymerizable sugar-acrylic product (e.g., tissue sealer or adhesive) is placed in contact with the damaged tissue along with any surgically acceptable patch or implant, if needed. When used to repair lacerated or separated tissue, such as by joining two or more tissue surfaces, the adhesive composition is applied to one or more of the tissue surfaces and then the surfaces are placed in contact with each other and adhesion occurs between them.

When used to repair herniated tissue, a surgically acceptable patch can be attached to the area of tissue surrounding the herniated tissue so as to cover the herniated area, thereby reinforcing the damaged tissue and repairing the defect. When attaching the patch to the surrounding tissue, the sugar-acrylic adhesive composition may be applied to either the patch, to the surrounding tissue, or to the patch after the patch has been placed on the herniated tissue. Once the patch and tissue are brought into contact with each other, adhesion occurs between them.

The surfaces to be adhered may be held together manually, or using other appropriate means, while the polymerization reaction is proceeding to completion. The time required for polymerization to occur can be on the order of a few seconds or minutes.

The tissue adhesives or sealers disclosed herein may be applied to any tissue surface and may be used in any customary method of tissue repair. The tissue adhesive or sealer is generally delivered to the site of administration in such a way that the individual components of the composition come into contact with one another for the first time at the site of administration, or within one hour preceding administration.

Thus, in one embodiment the tissue adhesive or sealer compositions are delivered to the site of administration using an apparatus that allows the components to be delivered separately. Such delivery systems may involve a multi-compartment device, including a multi-compartment spray device. Alternatively, the components of the adhesive or sealer can be delivered separately using any type of controllable extrusion system, or they can be delivered manually in the form of separate pastes, liquids or dry powders, and mixed together manually at the site of administration.

In an alternative embodiment, an environmentally benign adhesive is disclosed. The environmentally benign adhesive may have a sugar-acrylic monomer and a solvent selected to be environmentally benign. The environmentally benign adhesives may include polymerizable monomers manufactured according to any of the methods described herein. For example, the environmentally benign adhesives may include polymerizable sugar-acrylic monomers as exemplified by sugar-cyanoacrylates, protected sugar-(meth)acrylates, or sugar (meth)acrylates having unprotected carbohydrate moieties.

The environmentally benign adhesives may include a zero VOC solvent. Examples of zero VOC solvents include, but are not limited to acetone, methyl acetate, t-butyl acetate, p-chlorobenzotrifluoride, and combinations of these. The zero VOC solvent may be included in the environmentally benign adhesive in amount in a range from about 2 wt % to about 98% wt % solvent, about 4 wt % to about 40 wt % solvent, or about 5 wt % to about 20 wt % solvent.

V. TISSUE ENGINEERING USING SUGAR-ACRYLICS

The disclosure also relates to sugar-acrylic hydrogel products including a first polymerizable monomer having a carbohydrate moiety linked to an acrylate group. In one embodiment, the sugar-acrylic hydrogel product incorporating the sugar-acrylic monomer may be a tissue scaffolding material, a cell growth medium, a healing promoter material, an engineered tissue, an emulsion-templated porous polymer, or the like.

The sugar-acrylic hydrogel products may be provided as sugar-acrylic monomers dispersed in a biocompatible solvent that when used is formed into a polymeric hydrogel. In this embodiment, the hydrogel products typically include a cross-linking agent mixed with the polymerizable sugar-acrylic monomers. The cross-linking agent may be a bis, tris or poly-functional acrylic monomer that can be incorporated into the growing polymeric chain during polymerization. Providing the hydrogel compositions with sugar-acrylic moieties in monomeric form lowers the viscosity of the solutions, allows high concentrations of the monomer, produces mechanically robust hydrogels, allows for a wide variety of polymerization techniques to be used, and allows polymerization to be carried out "on demand." While there may be advantages to providing hydrogel product in monomeric form for some embodiments disclosed herein, the present disclosure also relates to hydrogel products in which the product is provided as an already polymerized hydrogel polymer.

The hydrogel products based on sugar-acrylics may provide several benefits in tissue engineering. For example, the pendant carbohydrate moiety provides an energy source for cell growth which other acrylics do not have. The sugar-acrylics tend to degrade to non-toxic chemicals that are more compatible with living cells.

The hydrogel products may be configured and implemented in a variety of tissue engineering applications. The hydrogel composition typically includes one or more biocompatible solvents and optionally any number of components that are configured to promote cell growth.

In one embodiment, the tissue engineering may relate to a porous scaffold manufactured from constructs with porogen nano/microparticles. The porous construct can be manufactured by first preparing a template using porogen nano/microparticles. The nano/microparticles may be salt, wax, organic, or polymeric nano/microparticles having a diameter in a range from 10 nanometers to about 200 micrometers, or about 100 nanometers to about 100 micrometers or about 200 nanometers to about 90 micrometers. The nano/microparticles can be made from synthetic polymers, naturally-occurring polymers, or mixtures of these. The nano/microparticles can be made from any material that can be removed from the construct through solvent extraction after the hydrogel has been polymerized around the porogen template of microparticles. An examples of suitable polymer microparticle material is (poly)methylmethacrylate (PMMA) while a suitable salt is sodium chloride, and a suitable wax is paraffin.

The porous scaffold may be formed by combining the nano/microparticles with one or more sugar-acrylic monomers as described herein and polymerizing the sugar-acrylic monomers in the presence of the microparticles. The microparticles may then be removed by solvent extraction to yield the porous scaffold of sugar-acrylic hydrogel having pores within about the range of the nano/microparticles. Where PMMA is the porogen microparticle material, the microparticles can be extracted from the sugar-acrylic hydrogel scaffold using an organic solvent such as acetone. Those skilled in the art will recognize the various solvent and nano/microsphere materials that are suitable for extracting the nano/microspheres without dissolving the hydrogel scaffolding.

In some embodiments, the hydrogel material has a thickness of at least 70 micrometers. For example, the sugar-acrylic hydrogel material may have a thickness between about 100 and 1000 micrometers, such as between about 100 micrometers and about 500 micrometers.

In one embodiment, the thickness of the sugar-acrylic hydrogel may be controlled by suspending the nano/microspheres between a set of plates and injecting a sugar-acrylic monomer solution in the spaces between the plates and between the nano/microspheres. In one embodiment, the thickness of the porous hydrogel scaffold may be controlled by compressing the scaffold between the plates. Additional details regarding manufacturing scaffolds between plates can be found in Ivirico, J. L. Escobar; Salmeron-Sanchez, M.; Ribelles, J. L. Gomez; Pradas, M. Monleon; Soria, J. M.; Gomes, M. E.; Reis, R. L.; Mano, J. F. "Proliferation and differentiation of goat bone marrow stromal cells in 3D scaffolds with tunable hydrophilicity", Journal of Biomedical Materials Research, Part B: Applied Biomaterials (2009), 91B(1), 277-286.

The present disclosure includes methods for forming scaffolding based on an emulsion-templated porous polymer (e.g., a high internal phase emulsion composition). The emulsion-templated porous polymer may be manufactured by dissolving one or more sugar-acrylic monomers in an aqueous phase and combining the aqueous phase with an organic phase and a surfactant to yield an intermediate reaction mixture. The one or more sugar-acrylic monomers in the intermediate reaction mixture may be polymerized to yield the emulsion-templated porous polymer. Additional details regarding emulsion-templated porous polymers can be found in U.S. Pat. No. 7,432,311 to Mezzenga, which is hereby incorporated herein by reference.

The present disclosure also includes methods for forming a hydrogel scaffold using a one or more sugar-acrylics and electrospinning. One or more sugar-acrylic monomers, a solvent, and a crosslinking agent are combined and loaded to an electro-spinning apparatus equipped with a high voltage statitron. The flow of the mixture may be controlled by a precision pump to maintain a steady flow. In one embodiment, the pump may be a peristaltic pump. The flow may be maintained in a range from about 0.1 ml/h to about 1.0 ml/h or in a range from about 0.4 ml/h to about 0.6 ml/h. A positive high voltage is applied to the sugar-acrylic monomer solution through the statitron. The charged solution forms sharp, conical-shaped drops in the positive electrode. The drops then narrow further, and scatter toward the negative electrode. The splashes of the solution droplets are vaporized as they fly in the air, and the polymers are converted into fibers (nanofibers). The electro-spun fibers are deposited on a rotating frame cylinder collector consisting of metal struts. When using the frame consisting of metal struts as the collector, the electrostatic forces drive the fibers to move towards the metal struts. Fibers of higher density are deposited on the metal struts while fibers of lesser density are deposited between the struts. The rotating speed of the cylinder collector is controlled by a stepping motor. The deposition time can be optimized to obtain fibrous mats with thicknesses in a range from about 200 micrometers to about 400 micrometers or about 250 micrometers to about 300 micrometers. The non-woven fibrous mats may be vacuum dried at room temperature to remove any solvent residue.

Additional details regarding electro-spinning may be found in US patent application publication numbers 20090074832 to Zussman and 20090246259 to Kita, which are both incorporated herein by reference.

In one embodiment the hydrogel products may be applied to a wound to promote wound healing. The hydrogel products may include compositions that elicit vascularization at a localized site, modulating localized wound healing response, and providing suitable means of developing a retrievable cell implantation device for cell-based therapeutics. Benefits of the wound healing products may include reduced scarring associated with degradation of bioerodible suture materials; improvement in the performance and long-term function of extravascular sensors; improvement in the rate of healing, durability, and mechanical properties around structural implants such as artificial joints and tendons; reduced pain and associated complications arising from post-surgical adhesions especially during abdominal or spinal injury; and improved integration between natural tissues and implanted structures (i.e. teeth, porous hydroxyapatite or ceramic materials for bone repair).

The hydrogel products used for wound healing may be polymerized and/or crosslinked outside the body and then implanted into a patient, or the hydrogel products can be allowed to polymerize and/or cross-link in situ. Irregular tissue defects, such as those common in chemical, thermal, or trauma wounds, which require rapid healing, also benefits from the ability to form in situ a bioactive hydrogel providing a cell attachment scaffold for tissue regeneration. An example method for delivering the liquid components of the hydrogel to the desired site for in situ formation involves using a multi-chamber syringe. Another method involves the use of the multi-chamber syringe with a single lumen catheter or needle containing a static mixing element where the components remain separated until injection into the site, but the high molecular weight components actually contact one another within the lumen of the catheter or needle during injection into the specified site. Where a sugar-cyanoacrylate monomer is used, it is possible to provide a single chamber delivery mechanism since the sugar-cyanoacrylates can cure in the presence of water.

The sugar-acrylic hydrogel may also be incorporated into wound dressings. Various types of bandages and wound dressings are known and used to protect wounds and burns. In one embodiment, the wound dressing is fabricated with a sugar-acrylic hydrogel polymer as described herein. The sugar-acrylic hydrogel acts as an absorbent material to remove wound exudate to dry the wound and facilitating healing. The sugar-acrylic hydrogel may also include one or more pharmacologically active agents such as antibiotics, local anesthetics, or the like.

The sugar-acrylic hydrogel can be designed to have a desired adhesiveness when incorporated into the bandage. In one embodiment, the carbohydrate moiety may be selected to minimize adhesion of the hydrogel polymer to avoid the situation where the bandage adheres to a patients wound thus causing pain or further injury upon removal. The sugar-acrylic hydrogel may have protecting groups to control adhesion and water swelling.

VI. EXAMPLES

The following examples describe methods for making sugar-acrylic monomers, polymers, adhesives, sealers, and engineered tissues. Examples 1-4 describe methods for making sugar-acrylic monomers and polymerization of the sugar-acrylic monomers to form hydrogels. Examples 5-8 describe methods for making sugar cyanoacrylate monomers and the polymerization of the sugar-cyanoacrylate monomers to form biocompatible polymers. Examples 9-11 describe methods for making sugar-acrylic monomers having protecting groups and the polymerization of the sugar-acrylic monomers to form biocompatible polymers. Examples 12-15 describe methods of making tissue adhesives and sealants from sugar-acrylic monomers. Examples 16-18 describe methods for constructing a template for a sugar-acrylic polymer scaffolds.

Example 1

Synthesis of Mannose Methacrylate Monomer

Example 1 describes the synthesis of a mannose methacrylate polymerizable monomer. Mannose substrate (7.2062 g, 0.04 mol), vinyl methacrylate (5.3822 g, 0.048 mol), *Candida Antarctica* lipase immobilized polymer (Novozym 4351, 4.03 g), and a few granules of BHT (to inhibit radical generation) are added to an Erlenmeyer flask containing 50 mL of acetone and sealed with a rubber septum. The flask is placed in a heated water stirring bath (50° C. and 150 rpm) and allowed to react for 5 days. Once finished, the yellow solution is filtered to remove the lipase enzyme from the monomer solution. Flash chromatography is performed (ethyl acetate: hexane:ethanol 7:2:1, Rf=0.38) on the crude residue to separate the desired monomer from any side reaction products. The relevant fractions are combined and rotary evaporation performed to remove solvent, which results in a pale yellow oil. The residue is dissolved in water for freeze-drying to yield the final, white powder product (70% yield). The reaction is shown below in Equation (1)

Equation (1)

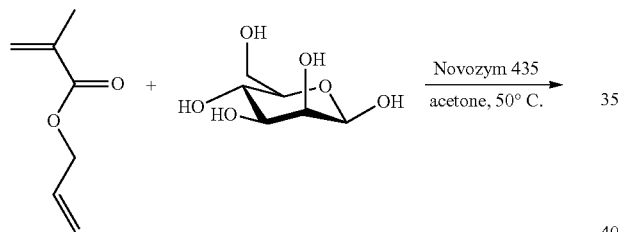

Example 2

Synthesis of Mannose Methacrylate Hydrogel

Example 2 describes the synthesis of a mannose methacrylate hydrogel using the mannose methacrylate of Example 1. Mannose methacrylate, 0.4 g, is dissolved into 3 mL of water. One drop (~0.030 g) of Darocure 1173 is added and well mixed into the solution, and then 0.04 g of poly(ethylene glycol) dimethacrylate crosslinker is added. The solution is purged of oxygen. The mannose methacrylate is polymerized by exposure to UV radiation (300-400 nm) for 3 minutes. The reaction is shown below in Equation (2)

Equation (2)

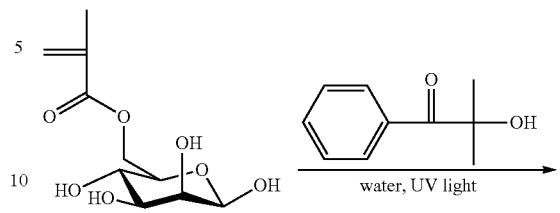

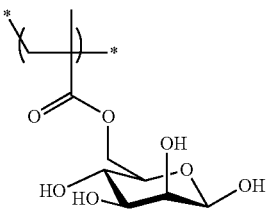

Example 3

Synthesis of β-D-N-Acetylgalactosamine Methacrylate Monomer

Example 3 describes the synthesis of a β-D-N-acetylgalactosamine methacrylate monomer. B-D-N-acetylgalactosamine substrate (0.04 mol), vinyl methacrylate (5.3822 g, 0.048 mol), *Candida Antarctica* lipase immobilized polymer (Novozym 4351, 4.03 g), and a few granules of BHT (to inhibit radical generation) are added to an Erlenmeyer flask containing 50 mL of acetone and sealed with a rubber septum. The flask is placed in a heated water stirring bath (50° C. and 150 rpm) and allowed to react for 5 days. Once finished, the yellow solution is filtered to remove the lipase enzyme from the monomer solution. Flash chromatography is performed (ethyl acetate:hexane:ethanol 7:2:1, Rf=0.38) on the crude residue to separate the desired monomer from any side reaction products. The relevant fractions are combined and rotary evaporation performed to remove solvent, which results in a pale yellow oil. The residue is dissolved in water for freeze-drying to yield the final, white powder product. The reaction is shown below in Formula (3)

Equation (3)

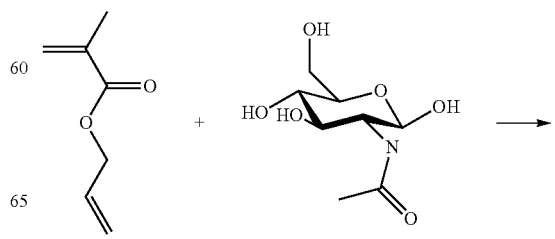

-continued

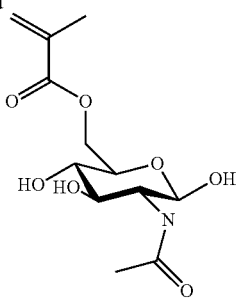

Example 4

Example 4 describes the copolymerization of mannose methacrylate made according to Example 1 and β-D-N-acetylgalactosamine methacrylate made according to Example 3. Mannose methacrylate from Example 1 and β-D-N-acetylgalactosamine methacrylate from Example 3 is dissolved in water. Darocure 1173 is added and well mixed into the solution, and then poly(ethylene glycol) dimethacrylate crosslinker is added. The solution is purged of oxygen. The mannose methacrylate and β-D-N-acetylgalactosamine methacrylate monomers are co-polymerized by exposure to UV radiation (300-400 nm) for 3 minutes. The resulting copolymer is a pseudo hyaluronic acrylic polymer hydrogel. The reaction is shown below in Equation 4.

Equation (4)

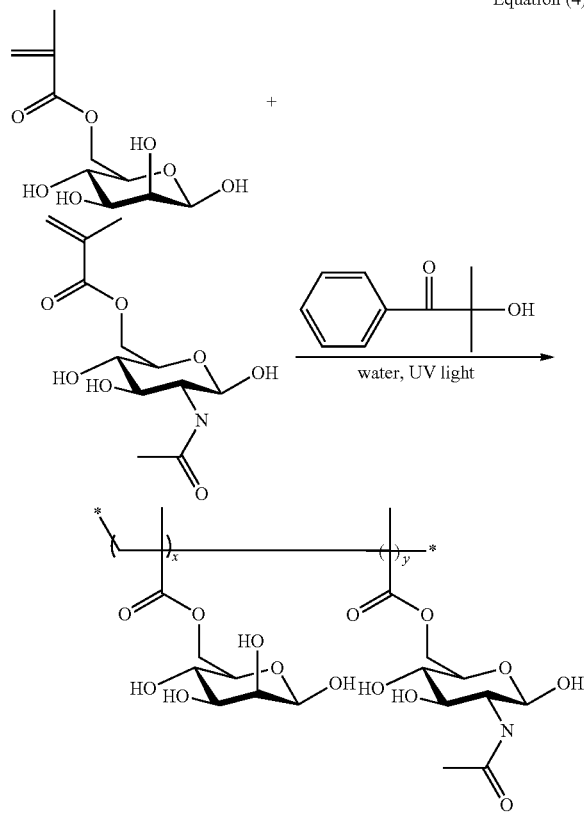

Example 5

Example 5 describes the synthesis of methyl tetraacetyl glucopyranuronate, which is an intermediate in the synthesis of 3,4,5-Triacetoxy-6-(2-cyano-acryloyloxy)-tetrahydro-pyran-2-carboxylic acid methyl ester. Sodium hydroxide (0.11 g) (or 4 mL of triethylamine) is dissolved in 300 mL of methanol. To this is added 40 g of glucuronolactone in 10 g increments. Add additional base is added if the pH drops below 8. The mixture is stirred for one hour and the methanol is then removed by rotary evaporation at 12 mmHg. The remaining methanol is removed by high vacuum overnight. Acetylation is performed by dissolving the product into 100 mL of pyridine and then addition of 150 mL of acetic anhydride. The solution became very hot upon the addition of acetic anhydride. The flask is then refrigerated overnight. Methyl tetra-O-acetyl-β-D-glucopyranuronate, 25 g, crystallized from the reaction. Yield of first crop of crystals is 75%. Yield can be increased by concentration of the mixture. The reaction is shown below in Equation 5.

Equation (5)

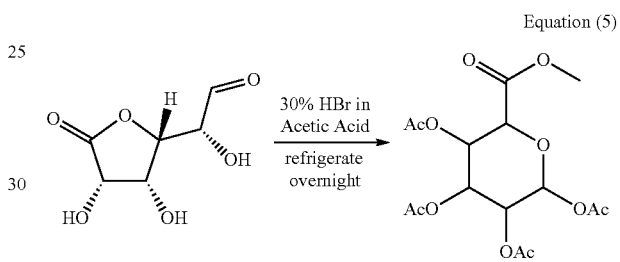

Example 6

Example 6 describes the synthesis of methyl 2,3,4-tri-O-acetyl-1bromo-1-deoxy-α-glucopyranuronate, which is an intermediate in the synthesis of 3,4,5-Triacetoxy-6-(2-cyano-acryloyloxy)-tetrahydro-pyran-2-carboxylic acid methyl ester. Methyl tetra-β-acetyl-β-D-glucopyranuronate produced according to Example 5, 20 g, is dissolved into 80 mL of 30% hydrogen bromide in acetic acid. The mixture, after solution, is refrigerated overnight. Chloroform, 75 mL, is added to the solution and with moderate stirring a saturated solution of sodium bicarbonate in water is slowly added until the acid wad neutralized. The chloroform is then extracted and dried with sodium sulfate. The chloroform is then removed by rotary evaporation. Absolute ethanol, 65 mL, is then added to the remaining syrup from which crystals began to separate. The mixture is allowed to stand in the refrigerator overnight. Colorless crystals of methyl 2,3,4-tri-O-acetyl-1-bromo-1-deoxy-α glucopyranuronate are obtained in a yield of 15 g. The reaction is shown below in Formula (6).

Equation (6)

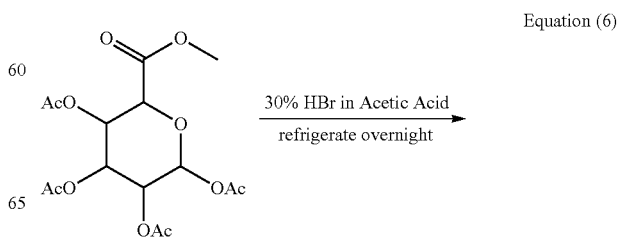

ⓘ indicates text missing or illegible when filed

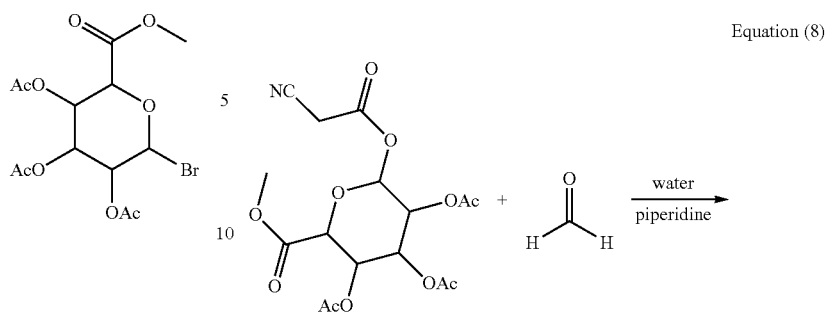

Example 7

Example 7 describes the synthesis of Methyl 2,3,4-tri-O-acetyl-1-cyanoacetate-β-glucopyranuronate, which is an intermediate in the synthesis of 3,4,5-Triacetoxy-6-(2-cyano-acryloyloxy)-tetrahydro-pyran-2-carboxylic acid methyl ester. Methyl 2,3,4-tri-O-acetyl-1-bromo-1-deoxy-α-glucopyranuronate produced according to the method illustrated in Example 6 is dissolved in dimethyl sulfoxide. To this is added two equivalents of cyanoacetic acid and cesium carbonate (2 equivalents). The mixture is heated to 30° C. for 3 h gave the corresponding methyl 2,3,4-tri-O-acetyl-1-cyanoacetate-β-glucopyranuronate in yields that range from 50-75%. The reaction in shown below in Equation 7

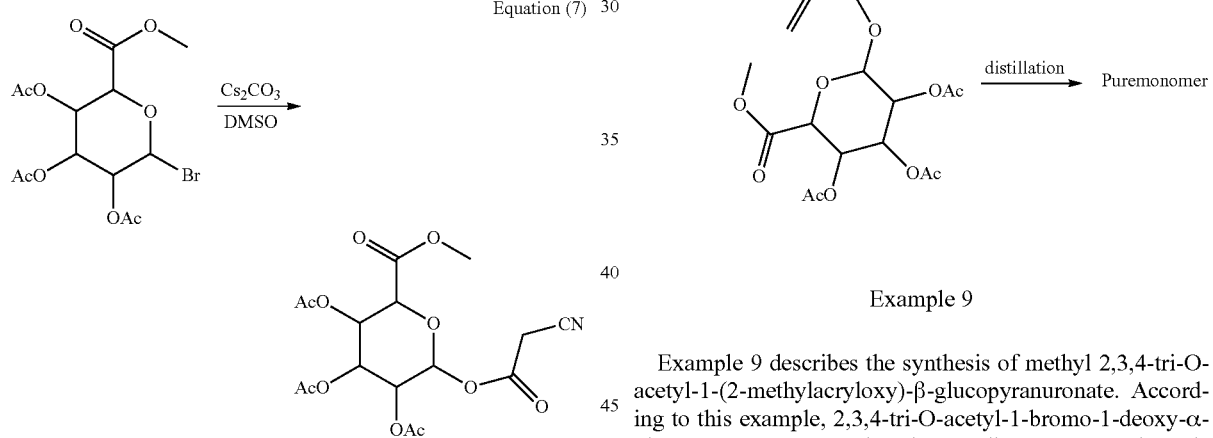

Equation (7)

Example 8

Example 8 describes the synthesis of 3,4,5-Triacetoxy-6-(2-cyano-acryloyloxy)-tetrahydro-pyran-2-carboxylic acid methyl ester. Cyanoacrylate monomers are produced by a large scale condensation process. The alkyl cyanoacetate, in this case is methyl 2,3,4-tri-O-acetyl-1-cyanoacetate-β-glucopyranuronate (produced according to Example 7) is condensed with formaldehyde in a reaction vessel. The resulting oligomers from this reaction are thermally depolymerized ("cracked") at 150-200° C., leading to a crude monomer and a crack residue, which is discarded. The pure monomer is produced from the high-vacuum distillation of the crude monomer and the residue remaining from this distillation is recycled back into the reaction vessel to complete the production cycle. A flow chart providing a simple overview of the manufacturing process is illustrated in Equation 8.

Equation (8)

Example 9

Example 9 describes the synthesis of methyl 2,3,4-tri-O-acetyl-1-(2-methylacryloxy)-β-glucopyranuronate. According to this example, 2,3,4-tri-O-acetyl-1-bromo-1-deoxy-α-glucopyranuronate produced according to Example 6 is dissolved in dimethyl sulfoxide. To this is added two equivalents of methacrylic acid and cesium carbonate. The mixture is heated to 30° C. for three hours, giving the corresponding methyl 2,3,4-tri-O-acetyl-1-(2-methylacryloxy)-β-glucopyranuronate in yields that range from 50-75% after purification on a silica column using 90% ethyl acetate/10% hexanes. The reaction is shown below in Formula 9

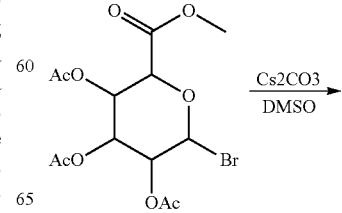

Equation (9)

-continued

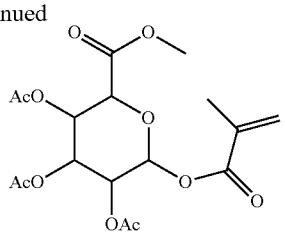

Example 10

Example 10 describes the synthesis of the monomer β-D-gluconic acid-3-methacrylate. Methyl 2,3,4-tri-O-acetyl-1-(2-methylacryloxy)-β-glucopyranuronate produced according to Example 9 can be selectively deprotected using the commercially available lipase AS Amano (LAS) and esterase from porcine liver (PLE). Incubation is started by the addition of a solution of Methyl 2,3,4-tri-O-acetyl-1-(2-methylacryloxy)-β-glucopyranuronate produced according to Example 9, 20 wt % in DMSO. The DMSO solution is added to 25 mM sodium citrate buffer (ratio 1:3) (pH5.0), LAS (1.6 g, 10 mg mL-1 incubation mixture) is dissolved at 40° C. and the mixture stirred magnetically for 3 hours. The reaction mixture is then filtered and the filtrate is loaded on an Amberlite XAD-4 column, which had been washed thoroughly with acetone and then equilibrated with water. The column is washed with water and then 30% CH3CN (50 mL). The hydrolyzed product of the methacrylate is eluted with ethyl acetate:hexanes:ethanol. Using a similar procedure the methyl ester is removed using PLE. The reaction is shown below in Equation 10 acrylate produced according to Example 10 can then be polymerized by itself in water or with other monomers such as β-D-N-acetylgalactosamine produced according to Example 3 to form a variety of hydrogels based upon carbohydrate methacrylate polymers.

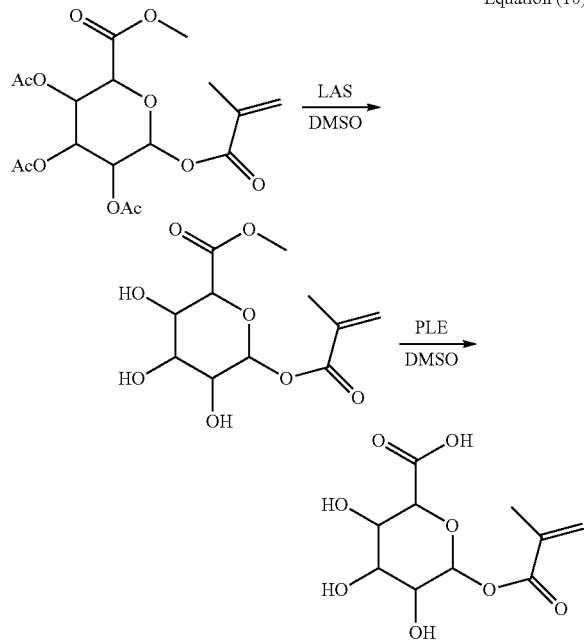

Equation (11)

R = H, CH₃

Example 12

Example 12 describes 3,4,5-Triacetoxy-6-(2-cyano-acryloyloxy)-tetrahydro-pyran-2-carboxylic acid methyl ester as a sealant used in surgery. 3,4,5-Triacetoxy-6-(2-cyano-acryloyloxy)-tetrahydro-pyran-2-carboxylic acid methyl ester produced according to Example 8 is mixed with 10 wt. % apple oil (ethyl isovalerate) to create a syrup that has the odor of apples. The sugar-cyanoacrylate can then be applied to the wound or in the area of surgery as a sealant or wound closure.

Example 13

Example 13 describes a method for making 3,4,5-Triacetoxy-6-(2-cyano-acryloyloxy)-tetrahydro-pyran-2-carboxylic acid methyl ester as an environmentally benign adhesive. According to this example, 3,4,5-Triacetoxy-6-(2-cyano-acryloyloxy)-tetrahydro-pyran-2-carboxylic acid methyl ester (produced according to Example 8) can be mixed with 10 wt. % of a zero VOC solvent such as acetone, methyl acetate, t-butyl acetate, p-chlorobenzotrifluoride to create a thick syrup. It may then be applied, to any two substrates that require adhering. In this way environmentally benign and biodegradable carbohydrate-cyanoacrylates can be created. As the pure monomer the sugar-cyanoacrylate can also be used without solvents by warming (~50° C.) between the two substrates to be combined. The sugar-cyanoacrylate then rapidly polymerizes, gluing the two substrates together.

Example 14

Example 14 describes Methyl 2,3,4-tri-O-acetyl-1-(2-methyl acryloxy)-β-glucopyranuronate as an environmentally benign adhesive. Methyl 2,3,4-tri-O-acetyl-1-(2-methylacryloxy)-β-glucopyranuronate produced according to Example 9 is dissolved into a zero VOC solvent such as acetone, methyl acetate, t-butyl acetate, p-chlorobenzotrifluoride. The solution of the carbohydrate-methacrylate may then be used to adhere plastics together.

Example 15

Example 15 describes Methyl 2,3,4-tri-O-acetyl-1-(2-methylacryloxy)-β-glucopyranuronate as an UV-curable environmentally benign adhesive. Methyl 2,3,4-tri-O-acetyl-1-(2-methylacryloxy)-β-glucopyranuronate produced according to Example 9 is dissolved in zero VOC solvents (examples include acetone, methyl acetate, t-butyl acetate, p-chlorobenzotrifluoride) to create a 90% monomer weight solution. A photo-initiator such as Darocur 1173 is added to create a UV-on demand curing adhesive that is environmentally benign. The adhesive has a very long pot life with certain photo-initiators, as they only decompose with UV light and not thermally. The glue may then be added to the substrates to be adhered together and exposed to UV light to polymerize the monomers. In this way a variety of substrates can be combined using an environmentally benign and biodegradable adhesive and a UV-curable environmentally benign adhesive.

Example 16

Example 16 describes a method for making a fibrous mat used for a cell growth scaffold by means of crosslinking and electro-spinning. An electrospinning apparatus is equipped with a high voltage statitron. Monomers such as β-D-N-acetylgalactosamine (produced according to Example 3) or mannose methacrylate (produced according to Example 1) are dissolved in water to prepare a 30% solution and added to a 2 mL glass syringe, which is attached with a clinically shaped metal capillary. The flow is controlled by a precision pump to maintain a steady flow of 0.5 mL/h from the capillary outlet. The electro-spun fibers are deposited on a rotating frame cylinder collector consisting of metal struts. When using the frame consisting of metal struts as the collector, the electrostatic forces drive the fibers to move towards the metal struts. Fibers of higher density are deposited on the metal struts while fibers of lesser density are deposited between the struts. The rotating speed of the cylinder collector is controlled by a stepping motor. The deposition time can be optimized to obtain fibrous mats with thicknesses of 250-300 µm. All the non-woven fibrous mats are vacuum-dried at room temperature for 3 days to completely remove any solvent residue prior to further characterization.

Example 17

Example 17 describes a method for making Poly(methyl methacrylate microparticles as porogen templates for constructing a scaffold with controlled porosity. Poly(methyl methacrylate) (PMMA) microparticles with diameter 90±10 µm are manufactured as porogen templates by introducing them between two plates whose distance can be controlled by adjusting the step of a coupled screw and heated at 180° C. for 30 min to obtain the first template. This template shows the highest porosity attainable with typical compaction values of 60-65% for random mono-sized spherical particles. To obtain scaffolds with controlled porosity, the thickness of the obtained disk is first measured; then the disk is replaced in the mould and compressed at 180° C. for half an hour. The degree of compression can be quantified by measuring the thickness diminution. A 30% solution of carbohydrate-methacrylate monomers in water or PBS buffer is created.

A water soluble photo-initiator such as Darocure 1173 is mix into the water/monomer solution. The water solution is then introduced in the empty space between the PMMA spheres after cooling the template to room temperature. The polymerization to create the hydrogel is carried out by exposing the system to UV light for three minutes. After polymerization takes place, the porogen template is removed by extraction with either acetone or methylene chloride. The porous sample is then extracted with ethanol to extract low molecular weight substances. Samples are then dried in vacuum to constant weight before characterization. The crosslinked porous samples can be re-swelled with water or PBS buffer.

Example 18

Example 18 describes a method for making a Emulsion-templated porous polymers structure used for cell growth medium. A water phase consisting of 70 wt. % carbohydrate-methacrylate monomers produced according to Example 1, 0.9 wt. % dimethacrylate crosslinkers, the photo-initiator Darocure 1173 (0.1%), and the surfactant sorbitan monooleate is added to a 250 ml three-necked round bottomed flask. The water phase is stirred continually at 300 rpm using a D-shaped PTFE paddle connected to an overhead stirrer. An organic phase consisting of cyclohexane is added over a period of two minutes using a peristaltic pump until a HIPE has formed. After addition of the organic phase is complete, the HIPE is stirred for a further period of one minute. The HIPE is then transferred to a glass centrifuge tube, which is irradiated with UV light for 5 minutes. Alternatively a thermo-initiator such as azobisisobutyronitrile can be used in lieu of the photo-initiator and the HIPE heated for 24 hours at 60° C. The resulting monolith can then be recovered from the tube and the low molecular weight impurities extracted in a Soxhlet apparatus with isopropyl alcohol for 24 hours and dried under vacuum.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

From the foregoing, it will be appreciated that various embodiments of the present disclosure have been described herein for purposes of illustration, and that various modifications may be made without departing from the scope and spirit of the present disclosure. Accordingly, the various embodiments disclosed herein are not intended to be limiting, with the true scope and spirit being indicated by the following claims.

The invention claimed is:

1. A biocompatible material providing a porous structure within which living tissue may grow, the biocompatible material comprising:

a sugar-acrylic polymer formed into a porous structure to allow ingrowth of living tissue, the sugar-acrylic polymer comprising at least one polymerized first acrylate monomer having a pendant carbohydrate moiety linked to an acrylate group of the first acrylate monomer, the pendant carbohydrate moiety comprising a derivative of a carbohydrate selected from the group consisting of allose, altrose, glucose, mannose, gulose, idose, galactose, talose, psicose, fructose, sorbose, tagatose, ribose, arabinose, xylose, lyxose, ribulose, xylulose, erythose, threose, erythrulose, glyceraldehydes, altro-heptulose, L-glycero-D-manno-heptose, and combinations thereof;

wherein the porous structure of the biocompatible material has a thickness from about 100 micrometers to about 1000 micrometers, and pores having a size from about 10 nm to about 200 micrometers.

2. The biocompatible material of claim 1, wherein the sugar-acrylic polymer has the formula (II):

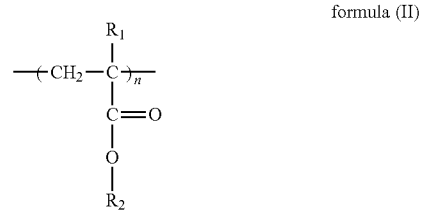

formula (II)

wherein n is an integer from 1 to 10,000, $R_1$ is H, alkyl, $-CF_3$, or $-CN$, and $R_2$ is a derivative of a carbohydrate selected from the group consisting of allose, altrose, glucose, mannose, gulose, idose, galactose, talose, psicose, fructose, sorbose, tagatose, ribose, arabinose, xylose, lyxose, ribulose, xylulose, erythose, threose, erythrulose, glyceraldehydes, altro-heptulose, L-glycero-D-manno-heptose, or a derivative thereof.

3. The biocompatible material of claim 1, wherein the sugar-acrylic polymer is a copolymer including a second polymerized acrylate monomer that is different from the first acrylate monomer.

4. The biocompatible material of claim 3, wherein the second polymerized acrylate monomer includes a second pendant carbohydrate moiety.

5. The biocompatible material of claim 3, wherein the copolymer is a pseudo hyaluronic acrylic polymer.

6. The biocompatible material of claim 1, wherein the porous structure comprises a fibrous mat, a scaffold material, a cell growth medium, and/or an emulsion-templated porous polymer.

7. A biocompatible material of claim 1, wherein the porous structure includes living cells disposed thereon.

8. The biocompatible material of claim 1, wherein the carbohydrate moiety is not a derivative of mannose or galactose.

9. The biocompatible material of claim 1, wherein one or more hydroxyl groups of the carbohydrate moiety are deriv-itized into a functional group selected from the group consisting of amide, ester, ether, silane, carbamate, ketal, acetal, hemiacetal, hemiketal, carbonate, and combinations thereof.

10. The biocompatible material of claim 7, wherein the carbohydrate moiety is linked to the acrylate monomer by a spacing group selected from the group consisting of alkyl, aryl, amino, thio, phosphine, alkene, alkyne, azo, substituted alkylene, unsubstituted alkylene, ether, polyol, ester, amide, imide, or a combination thereof.

11. The biocompatible material of claim 1, wherein the carbohydrate moiety is linked to the acrylate monomer by a spacing group, wherein the spacing group includes an O-link-age in which an ester bond links the carbohydrate moiety to the acrylate monomer.

12. The biocompatible material of claim 1, wherein the sugar-acrylic polymer is a copolymer of the first acrylate monomer and a copolymer selected from the group consisting of hydroxyethyl acrylate, hydroxyethyl methacrylate, hydox-ypropyl acrylate, hydoxypropyl methacrylate, styrene, acry-lamide, vinyl acetate, vinyl methacrylate, methylvinylether, trifluromethylvinylether, N-vinylpyrrolidone, methylvi-nylketone, maleic anhydride, and combinations thereof.

13. The biocompatible material of claim 1, wherein the sugar-acrylic polymer is a copolymer of the first acrylate monomer and a copolymer with more than one functionality, the copolymer being selected from the group consisting of divinylbenzene, ethylene glycol di(meth)acrylate, poly(eth-ylene glycol) di(meth)acrylate, and glycerol tri(meth)acry-late.

14. The biocompatible material of claim 5, wherein the pseudo hyaluronic acrylic polymer is an acrylic co-polymer including the first acrylate monomer with a glucose derivative as the pendant carbohydrate moiety and a second acrylate monomer with a β-D-N-acetylgalactosamine derivative as the second pendant carbohydrate moiety.

15. The biocompatible material of claim 14, wherein the first and second acrylate monomers alternate in the copoly-mer.

16. The biocompatible material of claim 14, having the structure:

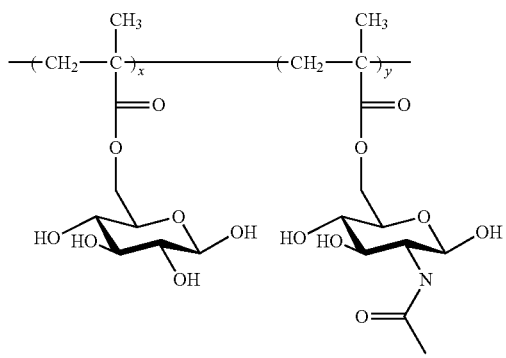

where x and y are each independently between 0.0001 and 99.9999.

17. The biocompatible material of claim 1, wherein the first acrylate monomer is a sugar-cyanoacrylate monomer.

18. The biocompatible material of claim 17, wherein the sugar-cyanoacrylate monomer has a structure selected from the group consisting of:

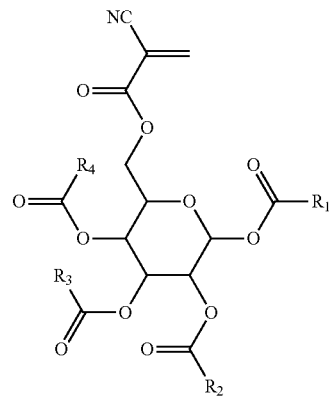

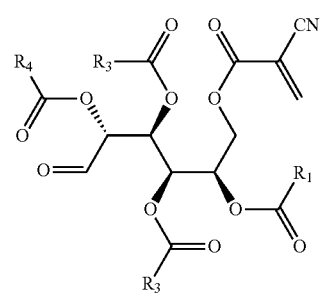

37
-continued
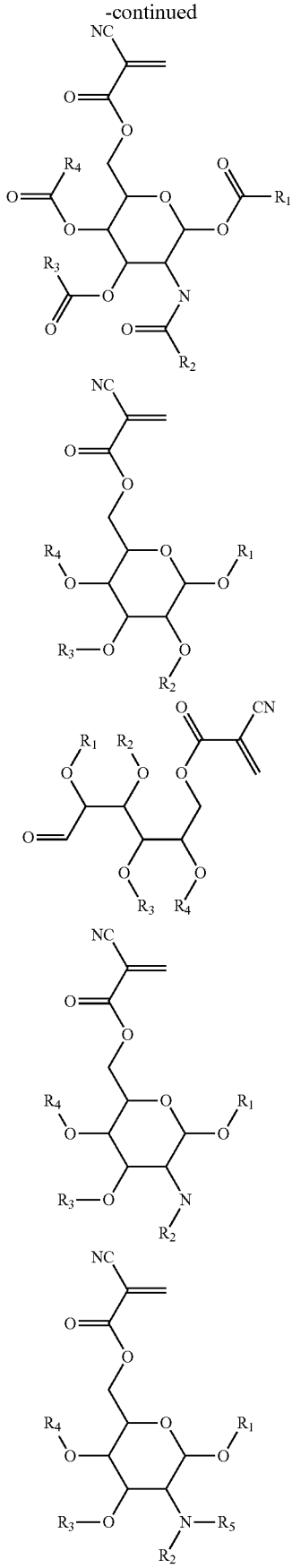
38
-continued
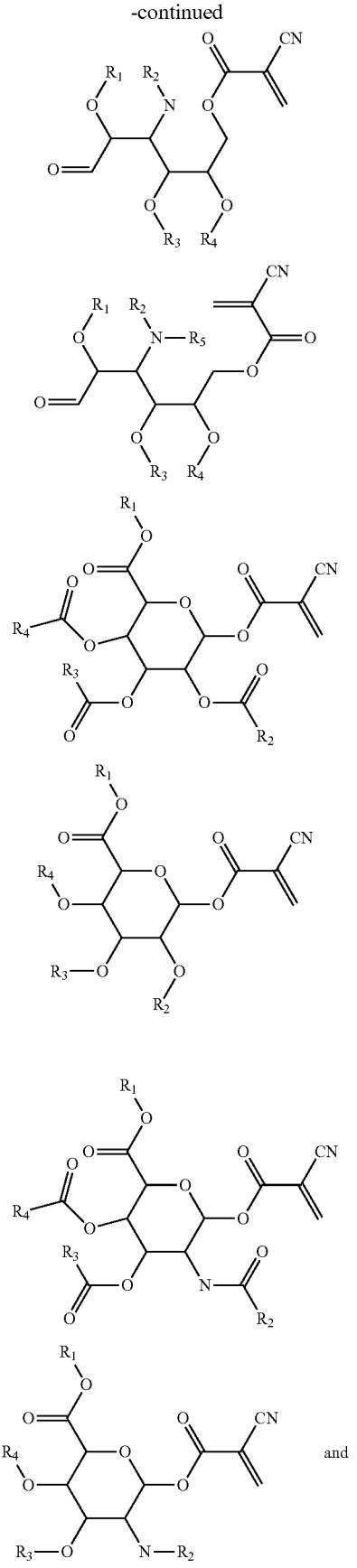
and

-continued

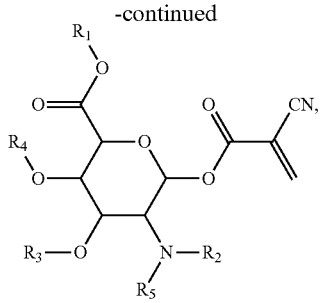

wherein $R_1$, $R_2$, $R_3$, and $R_4$ are independently an alkyl, heterocycle, cycle, carbocycle, or any atom other than hydrogen.

19. The biocompatible material of claim 1, wherein the porous structure of the biocompatible material has a compaction value of about 60-65%.

20. The biocompatible material of claim 1, wherein the pores have a size of about 90±10 micrometers.

21. A biocompatible material providing a porous structure within which living tissue may grow, the biocompatible material comprising:
a sugar-acrylic polymer formed into a porous structure to allow ingrowth of living tissue, the sugar-acrylic polymer comprising at least one polymerized first acrylate monomer having a pendant carbohydrate moiety linked to an acrylate group of the acrylate monomer, the pendant carbohydrate moiety comprising a derivative of a carbohydrate selected from the group consisting of allose, altrose, glucose, gulose, idose, talose, psicose, fructose, sorbose, tagatose; ribose, arabinose, xylose, lyxose, ribulose, xylulose, erythose, threose, erythrulose, glyceraldehydes, altro-heptulose, L-glycero-D-manno-heptose, and combinations thereof;
wherein the porous structure of the biocompatible material has a thickness from about 100 micrometers to about 1000 micrometers, and pores having a size from about 10 nm to about 200 micrometers.

* * * * *